United States Patent [19]

Weiss et al.

[11] Patent Number: 4,892,833
[45] Date of Patent: Jan. 9, 1990

[54] PROCESS AND A REAGENT KIT FOR THE DETERMINATION OF DIRECT AND TOTAL FILIRUBIN

[75] Inventors: Ludwig Weiss, Munich; Georg-Erich Hoffman, Grafrath, both of Fed. Rep. of Germany

[73] Assignee: Boehringer Mannheim GmbH, Mannheim, Fed. Rep. of Germany

[21] Appl. No.: 510,221

[22] Filed: Jul. 1, 1983

[30] Foreign Application Priority Data

Jul. 7, 1982 [DE] Fed. Rep. of Germany ....... 3225331

[51] Int. Cl.⁴ .............................................. C01N 33/72
[52] U.S. Cl. ........................................ 436/97; 422/61; 436/903
[58] Field of Search ..................... 436/97, 903; 422/61

[56] References Cited

U.S. PATENT DOCUMENTS

| | | | |
|---|---|---|---|
| 3,511,607 | 5/1970 | Green | 436/97 |
| 3,585,004 | 6/1971 | Mast | 436/97 X |
| 3,814,586 | 6/1974 | Fraser, Jr. et al. | 436/97 |
| 3,825,411 | 7/1974 | Morin | 436/97 |
| 4,468,467 | 8/1984 | Babb et al. | 436/903 X |

OTHER PUBLICATIONS

Hillman, Z. Klin. Chem. u. Klin. Biochem. 9, Jg., S. 273–274, Mai 1971.

Gedigk et al., Hoppe-Seylers Z. Physiol. Chem. 289, 261–271 (1952).

Gedigk et al., Chemical Abstracts, vol. 48, No. 18, No. 10815e, 1954.

Primary Examiner—Robert J. Hill, Jr.
Attorney, Agent, or Firm—Felfe & Lynch

[57] ABSTRACT

A process and reagent kit for the determination of direct and total bilirubin in body fluids by coupling the bilirubin with a diazonium salt and determining the extinction change thereby brought about, by usual methods.

The coupling is carried out in the presence of a buffer which adjusts the test solution to a weakly acidic to approximately neutral pH value preferably between pH 3.5 and 8. The diazonium salt is of the formula:

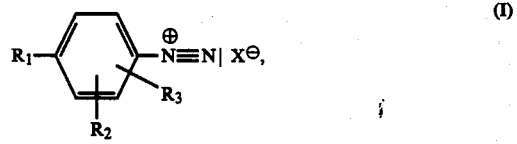

in which $R_1$ is a hydrogen or halogen atom or a lower alkyl, lower alkoxy or benzoylamino radical, $R_2$ is a hydrogen atom or a lower alkyl or lower alkoxy radical, $R_3$ is a hydrogen or halogen atom or a lower alkyl or lower alkoxy radical, whereby $R_1$ and $R_3$ do not simultaneously represent halogen atoms, and X is an anion forming a storage-stable salt with the diazonium cation.

13 Claims, No Drawings

PROCESS AND A REAGENT KIT FOR THE DETERMINATION OF DIRECT AND TOTAL FILIRUBIN

The present invention is concerned with a process and a reagent for the determination of direct and total bilirubin.

Bilirubin occurs in the human organism mainly as the most important breakdown product of haemoglobin. In the liver, bilirubin is partly conjugated with glucuronic acid. The glucuronated bilirubin is referred to as "direct" bilirubin and the part not conjugated with glucuronic acid is called "indirect" bilirubin. Normally, only small amounts of bilirubin are found in the blood, the normal concentrations being:

| for direct bilirubin: | up to 0.25 mg./100 ml. serum ($\triangleq$4.3 μmol/l.) |
|---|---|
| for indirect bilirubin: | up to 0.75 mg./100 ml. serum ($\triangleq$12.7 μmol/l.) |

In the healthy organism, bilirubin is excreted from the gall bladder with the biliary fluid into the intestine. However, this mechanism is disturbed in the case of various diseases. Thus, for example, in the case of increased haemoglobin breakdown, the glucuroniding system can be overloaded so that the ratio of direct/indirect bilirubin is changed. In the case of neonates, too, the glucuroniding capacity is underdeveloped, which also leads to displacements in the ratio between direct and indirect bilirubin In the case of liver cell damage, disturbances of the outflow in the biliary capillary or in the case of bile duct obstructions, the excretion of the bilirubin via the gall bladder into the intestine is reduced or completely blocked This leads to increased bilirubin concentrations in the blood Not only the absolute concentration of the bilirubin but also the ratio of direct/indirect bilirubin can thereby be influenced. Thus, from the measurement of both values, important diagnostic conclusions can be made regarding the nature and localisation of certain diseases of the liver-gall bladder-intestinal tract. Therefore, the determination of both bilirubin fractions is of especial importance in medical diagnosis. For this purpose, the total bilirubin is usually first determined, whereafter the direct bilirubin content is measured, the indirect bilirubin portion being given from the difference between the two values The most frequently carried out bilirubin detection reactions depend upon the coupling of bilirubin with diazonium salts. According to Jendrassik and Cleghorn (Biochem. Z., 289, 1/1937), for the determination of the direct bilirubin, 1 ml. of serum is mixed with 0.5 ml. of a diazo mixture which consists of 5 g. sulphanilic acid, 15 ml. concentrated hydrochloric acid and 0.25 ml. 0.5% sodium nitrite in water. In the case of this method of determination, it is especially disadvantageous that the reaction must be carried out in a strongly acidic medium.

For the determination of total bilirubin, caffeine and sodium benzoate are first added to the sample and only subsequently coupled with diazotised sulphanilic acid. The purpose of adding caffeine and sodium benzoate is to release indirect bilirubin from its bonding to albumin and to exclude disturbances due to protein precipitation which occurs without these additives.

However, with these additional materials, the determination reaction cannot be carried out in a strongly acidic medium as in the case of the determination of the direct bilirubin. On the contrary, it is necessary to work in the neutral or weakly acidic range. However, these reaction conditions have the disadvantage that brownish coloured by-products result with other component materials of the sample (for example with phenols) which, in numerous cases, disturb the test. The reagent solution itself is also not stable for a comparatively long period of time. Even in the absence of sample material, a substance results which is admittedly colourless in the acidic medium but even in the neutral range is yellow and in the alkaline range is red. In order to minimise errors which can arise due to these disturbances, very complicated steps have sometimes been suggested. For example, according to Jendrassik and Cleghorn, two different wavelengths are used or, after conclusion of the diazotisation reaction in the weakly acidic or neutral range, a transfer is made into an alkaline medium before the actual measurement of the test batch (Jendrassik and Grof, Biochem Z., 297, 81–89/1938)

All these methods of determination are unpleasant and impracticable to carry out. Furthermore, because of the numerous steps, they still involve great inexactitudes and errors. Therefore, attempts have been made to improve the methods of determination of direct and total bilirubin.

Thus, for example, attempts have been made to carry out the determination of total bilirubin in a strongly acidic medium. For this purpose, it was, above all, necessary to look for adjuvant substances which are able to break up the protein bond in a strongly acidic medium Thus, for example, Bartels and Boehmer (Z. Clin. Chem. Clin. Biochem., 7, 444/1969) have used dispersion agents and Winsten and Cehelyk (Clin. Chem. Acta, 25, 441/1969) have used dimethyl sulphoxide as a "solubiliser" for the indirect bilirubin in order subsequently to be able to carry out the total bilirubin determination in a strongly acidic medium in a manner analogous to that used for the determination of the direct bilirubin.

In spite of the numerous variants, the test methods for direct and total bilirubin previously described in the literature still do not satisfy the necessary requirements, as is shown by the poor agreements of the various methods (Jacobs et al., Clin Chem., 10, 433–439/1964). In particular, the strongly acidic, aggressive medium in which the previously known methods of determination had to be carried out in order to be able to achieve a reasonably practicable differentiation (loc. cit.) are disadvantageous for the practical carrying out of the test.

Therefore, it is an object of the present invention to provide a method of determination for direct and total bilirubin which can be carried out in a weakly acidic to approximately neutral pH range, is simple and easy to carry out and provides dependable values.

Surprisingly, we have found that the determination of direct and total bilirubin is possible in the weakly acidic to approximately neutral and in the absence of caffeine and sodium benzoate additives range when, for the coupling with the bilirubin, there are used diazonium salts substituted in a particular way, for example, diazotised 2-amino-5-chlorotoluene (Fast Red TR) or diazotised 2-methoxy-5-chloroaniline (Fast Red RC).

Thus, according to the present invention, there is provided a process for the determination of direct and total bilirubin in body fluids in which the bilirubin is coupled with a diazonium salt and the extinction change thereby brought about is measured according to known methods, wherein the coupling is carried out in the presence of a buffer which adjusts the test solution to a weakly acidic to approximately neutral pH value and, as coupling component, there is used a diazonium salt of the general formula:

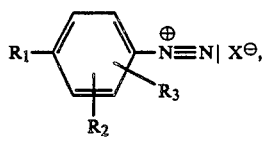

in which $R_1$ is a hydrogen or halogen atom or a lower alkyl, lower alkoxy or benzoylamino radical, $R_2$ is a hydrogen atom or a lower alkyl or lower alkoxy radical, $R_3$ is a hydrogen or halogen atom or a lower alkyl or lower alkoxy radical, whereby $R_1$ and $R_3$ do not simultaneously represent halogen atoms, and X is an anion forming a storage-stable salt with the diazonium cation.

The lower alkyl and lower alkoxy radicals in the definitions of the substituents $R_1$, $R_2$ and $R_3$ are to be understood to be radicals containing 1 to 5 and preferably 1 to 3 carbon atoms, the methyl, ethyl, methoxy and ethoxy radicals being especially preferred.

Halogen is to be understood to mean fluorine, chlorine, bromine or iodine, chlorine and bromine being especially preferred.

The anion forming a storage-stable salt with the diazonium cation is preferably the tetrafluoroborate or the tetrachlorozincate anion.

The diazonium salts used according to the present invention are either known compounds or can easily be prepared analogously to known compounds. Some of these diazonium salts have also already been used for the determination of bilirubin in a strongly acidic medium. However, it is surprising that coupling also takes place between bilirubin and the diazonium salts of general formula (I) in a weakly acidic to approximately neutral medium. In Z. Clin. Chem. Clin. Biochem., 9, 273/1971, it is, for example, expressly mentioned that a diazonium salt especially preferred in the sense of the present invention, i.e. diazotised 2-amino-5-chlorotoluene (Fast Red TR), does not react with bilirubin at a pH value of 5.2.

The present invention also provides an agent for carrying out the process according to the present invention for the determination of direct and total bilirubin, which agent contains the components necessary for the determination, i.e. diazonium salt and buffer, in the form of a solution, powder mixture, reagent tablet or lyophilisate or in the form of an absorbent carrier impregnated therewith.

For the determination of total and direct bilirubin, the agent can also contain a solubiliser.

According to the present invention, a buffer is advantageously employed which adjusts the test solution to a pH value in the range of 3.5 to 8.0. For the determination of direct bilirubin, a buffer is advantageously employed which is effective in the pH range of 3.5 to 6.0 and preferably of 4.3 to 5.7, whereas for the determination of total bilirubin, there is preferably used a buffer effective in the pH range of 5.5 to 8 and preferably of 6 to 7.

The buffers used are those which possess sufficient buffer capacity in the mentioned pH range. For the determination of direct bilirubin, it has proved to h = especially useful to use buffer systems such as citric acid/tris-(hydroxymethyl)-aminomethane, citric acid/aqueous sodium hydroxide solution, acetic acid/aqueous sodium hydroxide solution, potassium hydrogen phthalate/aqueous sodium hydroxide solution or phosphate buffer, the three first-mentioned buffer systems being especially preferred. For the determination of total bilirubin, it is especially preferable to use citric acid/tris-(hydroxymethyl)-aminomethane or hydrochloric acid/tris-(hydroxymethyl)-aminomethane Hydrochloric acid/imidazole buffer can also be employed.

For the determination of total bilirubin and of direct bilirubin, a solubiliser can also be added. For this purpose, dimethylformamide, dimethyl sulphoxide, tetrahydrofuran, dioxan and various glycols have proved to be especially useful, dimethylformamide being especially preferred For the determination of direct bilirubin, a non-ionic detergent, preferably Triton X 100 (Rohm & Haas, Philadelphia) can be added, the concentration of Triton X 100 being from about 0.1 to 1.0%. Further examples of non-ionic detergents which can be used include Tween 21 and Tween 40 (producer ICI), Tergitol 15-S-12 (Union Carbide Corp.) and BRIJ 78 (ICI).

For the determination of direct bilirubin and of total bilirubin, the sample to be determined is brought into contact with the diazonium salt, the buffer and possibly with the solubiliser. The coupling of the bilirubin in particular for the determination of total bilirubin, is accomplished in the absence of caffeine and sodium benzoate additives. The added materials can thereby be present as a solution, powder mixture, reagent tablet or lyophilisate or in the form of an absorbent carrier impregnated therewith. It is also possible to combine the various forms. Thus, for example, the buffer can be used as solution in an appropriate solvent and the diazonium salt in the form of a tablet The concentration of bilirubin to be measured in the test batch should be between 0.5 and 25 $\mu$mol/l. If necessary, the starting sample is to be appropriately diluted.

The amount of diazonium salt, buffer and possibly solubiliser used is so chosen that the final test solution contains the following concentrations diazonium salt: from 0.5 to 30 mmol/l. and preferably from 5 to 15 mmol/l., buffer: from 0.02 to 1.0 mol/l. and preferably from 0.05 to 0.3 mol/l., possibly added solubiliser from 0.1 to 4 mol/l. and preferably from 1 to 3 mol/l. in the case of measuring total bilirubin and from 0.01 to 0.1 mol/l. in the case of measuring direct bilirubin.

An important advantage of the process according to the present invention for the determination of direct and total bilirubin lies in the fact that the particular reaction conditions only differ by slight differences in the pH value of the test solution. Thus, both determinations can be carried out side by side with substantially identical reagents. The same diazonium salt is advantageously used for the determination of the direct and of the total bilirubin. The necessary differing pH value is achieved by slight variation in the composition of the buffer substances determining the pH value.

In practice, it is possible to proceed in such a manner that, for the determination of the direct and of the total bilirubin, in each case separate reagent compositions are prepared which contain the same diazonium salt but have differing compositions of the buffer components. It is also possible to proceed in such a manner that, for both determinations, a common reagent combination is prepared which contains the diazonium salt and a buffer for the adjustment of the pH value for one of the determination parameters. The pH value for the determination of the other parameter is adjusted by the addition of further appropriate buffer substances.

The agent according to the present invention for the determination of direct or total bilirubin in the form of a solution preferably contains all the reagents needed for the test. The solvent used can be water or a mixture of water with a water-soluble organic solvent, for example methanol, ethanol, acetone or dimethylformamide. For storage-stability reasons, it can be advantageous to divide the reagents needed for the test into two or more solutions which are only brought together immediately prior to carrying out the actual determination.

The agent according to the present invention in the form of a powder mixture or of a reagent tablet can be produced by mixing the necessary components of the test with conventional galenical additives and then granulated. Additives of this kind include carbohydrates, for example mono-, oligo- and polysaccharides, and sugar alcohols, for example mannitol, sorbitol and xylitol, and other soluble inert compounds, for example polyethylene glycols and polyvinylpyrrolidone. In general, the reagent tablets have an end weight of from about 20 to 200 mg. and preferably from 50 to 80 mg.

For the production of lyophilisates, a solution is freeze dried which, besides all the reagents needed for the determination, contains conventional structure formers, for example polyvinylpyrrolidone, and possibly further filler materials, for example mannitol, sorbitol or xylitol.

For the production of the agent according to the present invention for the determination of bilirubin in a form absorbed on an absorbent carrier, an absorbent carrier, preferably filter paper, cellulose or synthetic fibre fleece, is impregnated with solutions of the necessary test components in a readily volatile solvent, for example water, methanol, ethanol or acetone. The finished test papers can be used as such or stuck in known manner on to handles or preferably sealed between synthetic resin films and fine meshworks according to Federal Republic of Germany Patent Specification No. 21 18 455.

The individual reagents necessary for the determination of bilirubin can also be applied to a test strip. In this case, on to the test field containing the reagent components there is dropped a bilirubin-containing sample, for example serum, and, on the basis of the colour change which occurs, the bilirubin content of the sample is determined in known manner. The following Examples are given for the purpose of illustrating the present invention:

EXAMPLE 1.

1. Solutions:

Buffer solution 167 mmol tris-(hydroxymethyl)-aminomethane and 83 mmol citric acid are dissolved in distilled water to give a total volume of 1 liter. The solution has a pH value of 5.0.

Reaction solution 1 In 10 ml. of the above-mentioned buffer solution are dissolved 20 mg. Fast Red TR (diazotised 2-amino-5-chlorotoluene×½ZnCl$_2$). The solution is stable at ambient temperature for at least 24 hours.

Solution 2 (additional reagent for the determination of total bilirubin): 0.9 mol tris-(hydroxymethyl)-aminomethane are dissolved in distilled water to give a total volume of 1 liter.

2. Carrying out of the test:

Into microcuvettes (layer thickness 1 cm.) are pipetted at ambient temperature the various reagent solutions in the following way:

|  | A = direct bilirubin | | B = total bilirubin | |
|---|---|---|---|---|
|  | measured value | blank value | measured value | blank value |
| reaction solution 1 | 500 µl | — | 500 µl | — |
| buffer | — | 500 µl | — | 500 µl |
| dist. water | 50 µl | 50 µl | — | — |
| solution 2 | — | — | 50 µl | 50 µl |
| measurement of the extinction at 546 nm (E$_1$) | | | | |
| serum | 20 µl | 20 µl | 20 µl | 20 µl |
| measurement of the extinction after precisely 10 min. (E$_2$) at 546 nm. | | | | |

A reagent blank value is determined for each test series. This value is obtained by proceeding in a manner analogous to that described above for the "measurement value" but replacing the serum by the same amount of water.

3. Evaluation:

From the measured extinctions, the extinction differences are calculated as follows:

$$\Delta E_A = (E_2 - E_1)_{A \text{ measurement cuvette}} -$$
$$(E_2 - E_1)_{A \text{ blank cuvette}} -$$
$$(E_2 - E_1)_{A \text{ reagent blank value}}$$
$$\Delta E_B = (E_2 - E_1)_{B \text{ measurement cuvette}} -$$
$$(E_2 - E_1)_{B \text{ blank cuvette}} -$$
$$(E_2 - E_1)_{B \text{ reagent blank value}}$$

From the extinction differences obtained, the bilirubin content of the sample is determined as follows:

$\Delta E_A \times 0.93 =$ mmol direct bilirubin/l.

$\Delta E_B \times 0.93 =$ mmol total bilirubin/l.

EXAMPLE 2.

1. Solutions:

Buffer solution A (for direct bilirubin): A solution of 0.13 mol citric acid in water is mixed with 0.35 mol tris-(hydroxymethyl)-aminomethane and made up with water to a total volume of 1 liter. The solution has a pH value of 5.7.

Buffer solution B (for total bilirubin): A solution of 0.2 mol tris-(hydroxymethyl)-aminomethane in water is brought to pH 7.0 with hydrochloric acid. 50 ml. Dimethylformamide are added thereto and made up with distilled water to a total volume of 1 liter.

Reagent solution A or B: In 10 ml. each of buffer A or B are dissolved 40 mg. Fast Violet B (diazotised 6-benzoylamino-4-methoxy-3-aminotoluene ×½ZnCl$_{12}$).

2. Carrying out of the test:

Into cuvettes (layer thickness 1 cm.) are pipetted at ambient temperature the solutions stated below:

|  | A = direct bilirubin measurement value | B = total bilirubin measurement value |
| --- | --- | --- |
| reagent soln. A | 2 ml. | — |
| reagent soln. B | — | 2 ml. |
| measurement of the extinction at 578 nm (E$_1$) | | |
| serum | 0.08 ml. | 0.08 ml. |
| measurement of the extinction after precisely 10 min. (E$_2$) at 578 nm | | |

For each test series, a reagent blank value is determined. This value is obtained in that the procedure is carried out in a manner analogous to that described under "measurement value" but replacing the serum by the same amount of buffer A or B.

A blank value cuvette corresponding to Example 1, in which, instead of the reagent solution, a corresponding amount of buffer solution is used, is only necessary in the case of distinctly turbid or haemolytic sera.

3. Evaluation:

From the measured extinctions, extinction differences are calculated as follows:

$$\Delta E_A = (E_2 - E_1)_{A \text{ measurement cuvette}} - (E_2 - E_1)_{A \text{ reagent blank value}}$$
$$\Delta E_B = (E_2 - E_1)_{B \text{ measurement cuvette}} - (E_2 - E_1)_{B \text{ reagent blank value}}$$

From the extinction differences obtained, the bilirubin content of the sample is determined as follows:

$\Delta E_A \times 0.49 = $ mmol direct bilirubin/l.

$\Delta E_B \times 0.49 = $ mmol total bilirubin/l.

Alternatively, the bilirubin determination can also be carried out by reading off the extinction difference between the first and fifth minute after the start (kinetic measurement).

The bilirubin content in the sample can also be determined by measuring various serum samples with a definite, known bilirubin content and producing a calibration curve from which, for each extinction difference which has been obtained by the measurement of a sample with unknown bilirubin content, the corresponding bilirubin concentration can be read off.

Equal values for direct bilirubin are obtained as above when, instead of buffer solution A, there is used a citrate buffer with the addition of Triton X 100.

EXAMPLE 3.

1. Solutions:

Buffer solution: 73 mmol tris-(hydroxymethyl)-aminomethane and 49 mmol citric acid are dissolved in distilled water and made up to a total volume of 1 liter. The solution has a pH value of 4.3.

Reaction solution 1: In 10 ml. of this buffer are dissolved 20 mg. Fast Red RC (diazotised 2-methoxy-5chloroaniline ×½ZnCl$_2$). The solution is stable at ambient temperature for at least 24 hours.

Solution 2 (additional reagent for total bilirubin): 0.75 mol tris-(hydroxymethyl)-aminomethane is made up with distilled water to 1 liter.

2. Carryinq out of the test:

Into microcuvettes (layer thickness 1 cm.) are pipetted at ambient temperature the following solutions in the given manner:

|  | A = direct bilirubin | | B = total bilirubin | |
| --- | --- | --- | --- | --- |
|  | measurement value | blank value | measurement value | blank value |
| reaction soln. 1 | 500 µl | — | 500 µl | — |
| buffer | — | 500 µl | — | 500 µl |
| dist. water | 50 µl | 50 µl | — | — |
| solution 2 | — | — | 50 µl | 50 µl |
| measurement of the extinction at 546 nm (E$_1$) | | | | |
| serum | 20 µl | 20 µl | 20 µl | 20 µl |
| measurement of the extinction after precisely 10 min. at 546 nm (E$_2$) | | | | |

A reagent blank value is determined for each test series. This is obtained by proceeding in a manner analogous to that described above under "measurement value" but, instead of serum, using the same amount of water.

3. Evaluation:

From the measured extinctions, the extinction differences are calculated as follows:

$$\Delta E_A = (E_2 - E_1)_{A \text{ measurement cuvette}} - (E_2 - E_1)_{A \text{ blank value cuvette}} - (E_2 - E_1)_{A \text{ reagent blank value}}$$
$$\Delta E_B = (E_2 - E_1)_{B \text{ measurement cuvette}} - (E_2 - E_1)_{B \text{ blank value cuvette}} - (E_2 - E_1)_{B \text{ reagent blank value}}$$

From the extinction differences obtained, the bilirubin content of the sample can be determined as follows:

$\Delta E_A \times 0.83 = $ mmol direct bilirubin/l.

$\Delta E_B \times 0.83 = $ mmol total bilirubin/l.

Comparable results are obtained when, in the above-given reaction solution 1, 20 mg. Fast Red RC are replaced by 40 mg. Fast Blue BB (diazotised 2,5-diethoxy-4-benzoylaminoaniline ×½ZnCl$_2$) or 40 mg. Fast Blue RR (diazotised 2,5-dimethoxy-4-benzoylaminoaniline ×½ZnCl$_2$).

EXAMPLE 4.

Filter paper (for example VS 532 of the firm Binzer) is impregnated:

A: with a solution which contains 0.13 mol citric acid, 0.35 mol tris-(hydroxymethyl)-aminomethane and 4.0 g. Fast Violet B in 1 liter distilled water, B: with a solution which contains 0.2 mol tris-(hydroxymethyl)-aminomethane, 5% Triton X 100 and 4.0 g. Fast Violet B in 1 liter distilled water and has been adjusted to pH 7.0 with hydrochloric acid, and dried at 30° C.

For the determination of direct bilirubin, one drop of serum is applied to test strip A and for the determination of total bilirubin one drop of serum is applied to test strip B. After about 5 to 10 minutes, a colour change to brownish-violet can be observed. From the colour change, the content of bilirubin in the sample can be determined by comparison with a colour scale which has been produced with the help of serum samples of known bilirubin content. The colour change can also be determined with the help of a reflection photometer by measurement of the extinction change at 578 nm.

Similar results are obtained when impregnating filter papers with solutions which, instead of the above-mentioned Fast Violet B, contain Fast Red TR, Fast Red RC, Fast Blue BB or Fast Blue RR.

Fast Red TR=diazotised 2-amino-5-chlorotoluene
Fast Red RC=diazotised 2-methoxy-5-chloroaniline
Fast Blue BB=diazotised 2,5-diethoxy-4-benzoylamino aniline ×½ZnCl$_2$
Fast Blue RR =diazotised 2,5-dimethoxy-4-benzoylamino aniline ×½ZnCl$_2$ It will be understood that the specification and examples are illustrative but not limitative of the present invention and that other embodiments within the spirit and scope of the invention will suggest themselves to those skilled on the art.

What is claimed is:

1. A process for the determination of bilirubin in body fluids, comprising the steps of
   adjusting the pH of a first test solution sample with a buffer to a pH range of 4.3 to 5.7 and thereafter coupling the bilirubin with a diazonium salt of the formula:

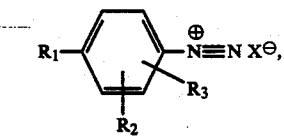

(I)

in which R$_1$ is a hydrogen or halogen atom or a lower alkyl, lower alkoxy or benzoylamino radical, R$_2$ is a hydrogen atom or a lower alkyl or lower alkoxy radical, R$_3$ is a hydrogen or halogen atom or a lower alkyl or lower alkoxy radical, whereby R$_1$ and R$_3$ do not simultaneously represent halogen atoms, and X is an anion forming a storage-stable salt with the diazonium cation, to determine direct bilirubin; and
   adjusting the pH of a second test solution sample to a pH range from 6 to 7 and thereafter coupling the bilirubin with said diazonium salt in the absence of caffeine and sodium benzoate additives, to determine total bilirubin;
   determining the difference between total and direct bilirubin as a measure of the amount of indirect bilirubin present.

2. The process of claim 1 wherein the diazonium salt is used in a concentration of 0.5 to 30 mmol/l. of test solution and the buffer is used in a concentration of 0.02 to 1 mmol/l. of test solution.

3. The process of claim 2, wherein the diazonium salt is used in a concentration of 5 to 15 mmol/l. of test solution and the buffer is used in a concentration of 0.05 to 0.3 mmol/l. of test solution.

4. The process of claim 1 wherein a solubilizing substance is additionally added.

5. The process of claim 4, wherein the solubilizing substance is dimethylformamide.

6. The process of claim 4 wherein the concentration of the solubilizing substance in the test solution is, in the case of the determination of total bilirubin 1 to 3 mol/l. and, in the case of the determination of direct bilirubin, 0.01 to 0.1 mmol/l.

7. The process of claim 1 wherein the buffer is citric acid/tris-(hydroxymethyl)-aminomethane; citric acid-/aqueous sodium hydroxide solution; acetic acid/aqueous sodium hydroxide solution; potassium hydrogen phthalate/aqueous sodium hydroxide solution; phosphate buffer, hydrochloric acid/tris-(hydroxymethyl)-amino-methane or hydrochloric acid/imidazole buffer.

8. A reagent kit for the determination of bilirubin consisting essentially of
   a buffer system effective in a pH range of 4.3 to 5.7 and a diazonium salt of the formula:

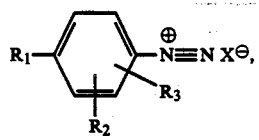

(I)

in which R$_1$ is a hydrogen or halogen atom or a lower alkyl, lower alkoxy or benzoyl amino radical, R$_2$ is a hydrogen atom or a lower alkyl or lower alkoxy radical, R$_3$ is a hydrogen or halogen atom or a lower alkyl or lower alkoxy radical, whereby R$_1$ and R$_3$ do not simultaneously represent halogen atoms, and X is an anion forming a storage-stable salt with the diazonium cation; for use in determining direct bilirubin; and
   a buffer system effective in a pH range of 6–7 and said diazonium salt; for use in determining total bilirubin; indirect bilirubin being determinable from the difference between total and direct bilirubin.

9. The reagent kit of claim 8 wherein the buffer is citric acid/tris-(hydroxymethyl)-aminomethane; citric acid/aqueous sodium hydroxide solution; acetic acid-/aqueous sodium hydroxide solution; potassium hydrogen phthalate/aqueous sodium hydroxide solution; phosphate buffer, hydrochloric acid/tris-(hydroxymethyl)-amino-methane or hydrochloric acid/imidazole buffer.

10. The reagent kit of claim 8 wherein said diazonium salt is Fast Violet B, Fast Red TR, Fast Red RC, Fast Blue BB or Fast Blue RR.

11. The reagent kit of claim 8 wherein the buffer is citric acid/tris-(hydroxymethyl)-aminomethane; citric acid/aqueous sodium hydroxide solution; acetic acid-/aqueous sodium hydroxide solution; potassium hydrogen phthalate/aqueous sodium hydroxide solution; phosphate buffer, hydrochloric acid/tris-(hydroxymethyl)-amino-methane or hydrochloric acid/imidazole buffer and the diazonium salt is Fast Violet B, Fast Red RC, Fast Blue BB or Fast Blue RR.

12. A reagent kit for the determination of bilirubin consisting essentially of
   a solubilizing agent,
   a buffer system effective in a pH range of 4.3 to 5.7 and a diazonium salt of the formula:

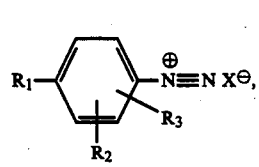

(I)

in which R$_1$ is a hydrogen or halogen atom or a lower alkyl, lower alkoxy or benzolyamino radical, R$_2$ is a hydrogen atom or a lower alkyl or lower alkyl alkoxy radical, R$_3$ is a hydrogen or halogen atom or a lower alkyl or lower alkoxy radical, whereby $R_1$ and $R_3$ do not simultaneously represent halogen atoms, and X is an anion forming a storage-stable salt with the diazonium cation; for use in determining direct bilirubin and a buffer system effective in a pH range of 6–7 and said diazonium salt; for use in determining total bilirubin; indirect bilirubin being determinable from the difference between total and direct bilirubin.

13. The reagent kit of claim 12 wherein the solubilizing agent is dimethylformamide.